United States Patent [19]

Anderson

[11] Plant 4,316

[45] Oct. 17, 1978

[54] PLUM TREE (25-P-40)

[75] Inventor: Frederic W. Anderson, Merced, Calif.

[73] Assignee: Reedley Nursery, Inc., Reedley, Calif.

[21] Appl. No.: 867,369

[22] Filed: Jan. 6, 1978

[51] Int. Cl.[2] ..... A01H 5/03

[52] U.S. Cl. ..... Plt./38

[58] Field of Search ..... Plt./38

*Primary Examiner*—Robert E. Bagwill

*Attorney, Agent, or Firm*—Roger B. Webster

[57] ABSTRACT

A plum tree which is medium size, medium vigorous, spreading in form, open in growth, foliated with medium size, obovate, acutely pointed leaves having a crenate margin, medium length petiole, and alternate, globose glands, and a regular and productive bearer of medium size, uniform, symmetrical, globose, clingstone fruit having yellow skin partially overspread with red, and yellow flesh.

1 Drawing Figure

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of plum tree resulted from my endeavors in the conduct of such plant breeding program; such variety being embraced by Class 38, Plants, of the U.S. Patent Office Manual of Classification.

2. Prior Varieties

Among the existent varieties of plum trees which are known to me are those mentioned herein for the purpose of comparison; to-wit, Cassellman (unpatented) and Rosemary (U.S. Plant Pat. No. 3,797).

ORIGIN OF THE VARIETY

The present variety of plum tree was originated by me in my experimental nursery and orchard, located as aforesaid, as a cross between two unnamed varieties of plum trees which existed in said orchard. Seedlings resulting from such cross were maintained by me under careful and continuing observation,and—in maturity—one of such seedlings (and which is the present variety) evidenced certain novel and desirable characteristics for commercial production. I, therefore, selected such one seedling for asexual reproduction.

ASEXUAL REPRODUCTION OF THE VARIETY

Subsequent to origination and selection by me of the present variety of plum tree, I asexually reproduced it by top-working on mature trees in my said experimental orchard, and—in maturity—such reproductions ran true to the original tree in all respects.

SUMMARY OF THE VARIETY

The herein-claimed new and distinct variety of plum tree is medium size, medium vigorous, spreading in form, open in growth, foliated with medium size, obovate, acutely pointed leaves having a crenate margin, medium length petiole, and alternate, globose glands, and a regular and productive bearer of medium size, uniform, symmetrical, globose, clingstone fruit having yellow skin partially overspread with red, and yellow flesh.

The herein-claimed plum tree, as above, is particularly characterized—as to novelty—by a harvest which extends later than most commercial plum varieties, and which is about two weeks later than the Cassellman and the Rosemary; and—in further comparison—the clingstone fruit of the present variety has less red exterior color, but a brighter yellow skin and flesh color, and is sweeter in all stages of maturity than the Cassellman, Rosemary, and other oriental species of plums.

BRIEF DESCRIPTION OF THE DRAWING

The drawing is an illustration, by photographic reproduction in color, of a twig with leaves, and separate fruit; one of the latter being partially cut away to expose the flesh.

DESCRIPTION OF THE VARIETY

The botanical details of this new and distinct variety of plum tree—with color definitions (except those in common color terms) referenced to Maerz and Paul Dictionary of Colors—are as follows:

Tree:
- *Size.*—Medium.
- *Vigor.*—Medium.
- *Form.*—Spreading.
- *Growth.*—Open.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Brown to gray.

Leaves:
- *Size.*—Medium. Average length — 4½". Average width — 2".
- *Form.*—Obovate. Acutely pointed.
- *Thickness.*—Medium.
- *Texture.*—Smooth.
- *Margin.*—Crenate.
- *Petiole.*—Medium length — average ¾". Medium thickness.

*Glands.*—Average number and position — usually 1 on petiole and 1 or 2 on base of blade. Alternate. Medium to small. Globose.

*Color.*—Top side — Medium green (22-K-6). Under side — Lighter green (21-L-5).

Flower buds:

*Length.*—Short.

*Form.*—Obtuse.

Flowers:

*Date of first bloom.*—Mar. 3rd, 1977.

*Date of full bloom.*—Mar. 10th, 1977. Medium, as compared with other varieties.

Fruit:

*Maturity when described.*—Eating ripe — Oct. 10th, 1977.

*Date of first picking.*—Aug. 15th, 1977.

*Date of last picking.*—Oct. 25th, 1977.

*Size.*—Uniform. Medium. Average diameter axially — 2". Average transversely in suture plane — 2-1/16".

*Form.*—Uniform. Symmetrical. Globose.

*Suture.*—A shallow, inconspicuous line extending from base to apex, with no depression beyond pistil point.

*Ventral surface.*—Rounded. Strongly lipped.

*Cavity.*—Rounded.

*Base.*—Rounded.

*Apex.*—Short.

*Pistil point.*—Wanting.

Skin:

*Thickness.*—Medium.

*Texture.*—Medium.

*Tendency to crack.*—None noted.

*Down.*—Wanting.

*Color.*—Yellow (12-L-4) partially overspread red (4-L-10) shading to darker red (5-L-6).

Flesh:

*Juice.*—Moderate.

*Texture.*—Firm. Meaty. Melting.

*Ripens.*—Evenly.

*Flavor.*—Subacid. Mild. Delicate.

*Aroma.*—Wanting.

*Eating quality.*—Good to best.

*Color.*—Yellow (11-L-6). Surface of pit cavity — Yellow.

Stone:

*Type.*—Cling.

*Size.*—Small. Average length — 1". Average breadth — $\frac{3}{8}$". Average thickness — $\frac{1}{2}$".

*Form.*—Oblong.

*Base.*—Straight.

*Hilum.*—Narrow

*Apex.*—Acute.

*Sides.*—Equal.

*Ventral edge.*—Thin.

*Dorsal edge.*—Narrow.

*Tendency to split.*—Very slight.

*Color.*—Brown (15-A-12)

Use: Market. Dessert. Canning.

Keeping quality: Very good.

Resistance to insects and disease: No unusual susceptibilities noted.

Shipping quality: Good to medium.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, characterized—in comparison to the Cassellman and Rosemary—by a harvest about 2 weeks later, and by clingstone fruit having less exterior red color, but brighter yellow skin and flesh, and much sweeter flavor.

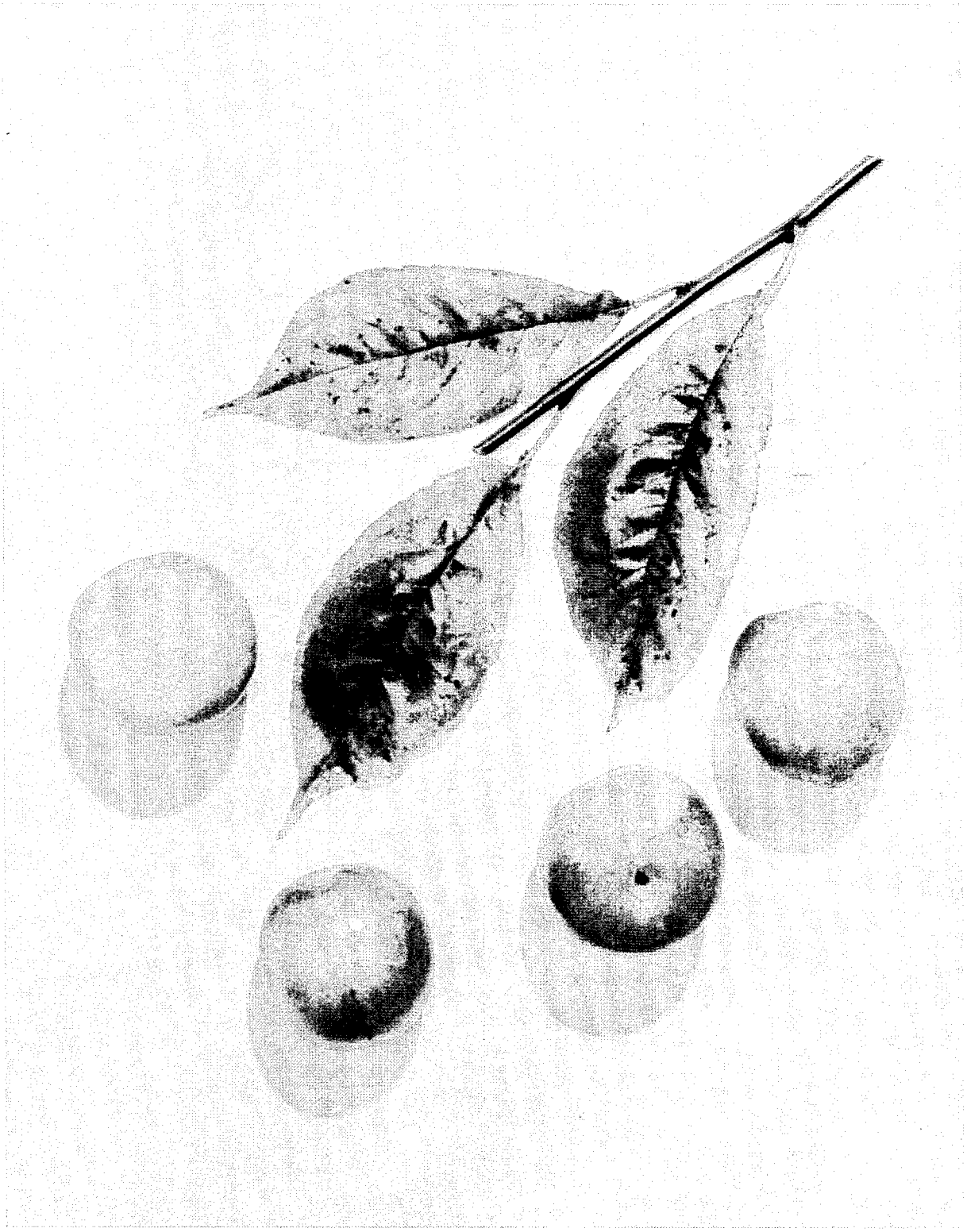

* * * * *